United States Patent
Eidelman et al.

(10) Patent No.: US 9,737,724 B2
(45) Date of Patent: Aug. 22, 2017

(54) HERMETICALLY SEALED ELECTROLYTIC CAPACITOR

(75) Inventors: Alex Eidelman, Beer-Sheva (IL); Stephen Breithaupt, N. Bennington, VT (US); Sarah Lastella, Troy, NY (US); Edward Fairfield, Hopkinton, NH (US); Vicki Segel, Beer-Sheva (IL); Pavel Vaisman, Beer-Sheva (IL); Hila Eshel, Beer-Sheva (IL); John Evans, Pownal, VT (US); Ilia Statkov, Beer-Sheva (IL); Nola Evans, legal representative, Pownal, VT (US); Leonid Statkov, legal representative, Beer-Sheva (IL); Tatyana Raich, legal representative, Beer-Shiva (IL)

(73) Assignee: Vishay Sprague, Inc., Malvern, PA (US)

( * ) Notice: Subject to any disclaimer, the term of this patent is extended or adjusted under 35 U.S.C. 154(b) by 638 days.

(21) Appl. No.: 13/983,538

(22) PCT Filed: Feb. 3, 2012

(86) PCT No.: PCT/US2012/023796
§ 371 (c)(1),
(2), (4) Date: Jul. 17, 2014

(87) PCT Pub. No.: WO2012/106611
PCT Pub. Date: Aug. 9, 2012

(65) Prior Publication Data
US 2015/0127060 A1    May 7, 2015

(51) Int. Cl.
*A61N 1/39* (2006.01)
*H01G 9/06* (2006.01)
(Continued)

(52) U.S. Cl.
CPC ......... *A61N 1/3975* (2013.01); *A61N 1/3956* (2013.01); *A61N 1/3968* (2013.01);
(Continued)

(58) Field of Classification Search
CPC  H01G 9/035; H01G 9/08; H01G 9/10; H01G 9/06; H01G 9/0425; H01G 9/0029
See application file for complete search history.

(56) References Cited

U.S. PATENT DOCUMENTS 2,089,686 A    8/1937   Clark et al.
3,138,746 A    6/1964   Burger et al.
(Continued)

FOREIGN PATENT DOCUMENTS

CN    101496197 A    7/2009
EP    1053763 A2     11/2000
(Continued)

OTHER PUBLICATIONS

International Search Report for corresponding International Application No. PCT/US2012/023796.

*Primary Examiner* — David M Sinclair
(74) *Attorney, Agent, or Firm* — Volpe and Koenig, P.C.

(57) ABSTRACT

A hermetically sealed capacitor and method of manufacturing are provided. The hermetically sealed capacitor includes an anode element having an anode wire and a feed through barrel, a cathode element, a first case portion having a first opening portion and a second case portion having a second opening portion. The first and second opening portions form an opening configured to mate with the feed through barrel. The first opening portion may include a slot portion configured to receive the feed through barrel. The hermetically sealed capacitor may also include electrolytic solution disposed between the first and second case portions.

30 Claims, 6 Drawing Sheets

(51) Int. Cl.
  *H01G 9/10* (2006.01)
  *H01G 9/00* (2006.01)
  *H01G 9/035* (2006.01)
  *H01G 9/042* (2006.01)

(52) U.S. Cl.
  CPC .......... *H01G 9/0029* (2013.01); *H01G 9/035* (2013.01); *H01G 9/0425* (2013.01); *H01G 9/06* (2013.01); *H01G 9/10* (2013.01); *Y10T 29/417* (2015.01)

(56) References Cited

U.S. PATENT DOCUMENTS

| | | | |
|---|---|---|---|
| 3,275,902 A | 9/1966 | McHugh et al. | |
| 3,624,460 A | 11/1971 | Correll | |
| 4,025,827 A | 5/1977 | Pellerin et al. | |
| 4,987,519 A | 1/1991 | Hutchins et al. | |
| 5,131,388 A * | 7/1992 | Pless | A61N 1/3956 607/5 |
| 5,245,513 A | 9/1993 | Maijers et al. | |
| 5,338,472 A | 8/1994 | Yokoyama et al. | |
| 5,391,186 A * | 2/1995 | Kroll | A61N 1/3956 607/5 |
| 5,507,966 A | 4/1996 | Liu | |
| 6,157,531 A | 12/2000 | Breyen et al. | |
| 6,219,222 B1 | 4/2001 | Shah et al. | |
| 6,231,993 B1 | 5/2001 | Stephenson et al. | |
| 6,334,879 B1 | 1/2002 | Muffoletto et al. | |
| 6,509,588 B1 | 1/2003 | Barr et al. | |
| 6,560,089 B2 | 5/2003 | Miltich et al. | |
| 6,571,126 B1 | 5/2003 | O'Phelan et al. | |
| 6,586,134 B2 | 7/2003 | Skoumpris | |
| 6,678,559 B1 * | 1/2004 | Breyen | A61N 1/375 361/503 |
| 6,687,118 B1 | 2/2004 | O'Phelan et al. | |
| 6,807,048 B1 | 10/2004 | Nielsen et al. | |
| 6,850,405 B1 * | 2/2005 | Mileham | A61N 1/375 29/25.41 |
| 6,859,353 B2 | 2/2005 | Elliott et al. | |
| 6,946,220 B2 | 9/2005 | Probst et al. | |
| 6,957,103 B2 | 10/2005 | Schmidt et al. | |
| 7,012,799 B2 | 3/2006 | Muffoletto et al. | |
| 7,038,901 B2 | 5/2006 | Muffoletto et al. | |
| 7,085,126 B2 | 8/2006 | Muffoletto et al. | |
| 7,164,574 B2 | 1/2007 | Barr et al. | |
| 7,271,994 B2 | 9/2007 | Stemen et al. | |
| 7,355,840 B2 | 4/2008 | Doffing et al. | |
| 7,483,260 B2 | 1/2009 | Ziarniak et al. | |
| 7,710,713 B2 | 5/2010 | Restorff et al. | |
| 7,715,174 B1 * | 5/2010 | Beauvais | A61N 1/375 361/516 |
| 7,813,107 B1 | 10/2010 | Druding et al. | |
| 7,983,022 B2 | 7/2011 | O'Connor et al. | |
| 8,477,479 B2 | 7/2013 | Pease et al. | |
| 8,687,347 B2 | 4/2014 | Bates et al. | |
| 9,105,401 B2 | 8/2015 | Dreissig et al. | |
| 2005/0177193 A1 * | 8/2005 | Nielsen | A61N 1/375 607/5 |
| 2005/0180094 A1 * | 8/2005 | Muffoletto | H01G 9/035 361/504 |
| 2006/0012945 A1 * | 1/2006 | Doffing | H01G 9/14 361/517 |
| 2006/0018079 A1 | 1/2006 | Barr et al. | |
| 2006/0279907 A1 | 12/2006 | Doffing et al. | |
| 2008/0026286 A1 | 1/2008 | Cui et al. | |
| 2008/0068779 A1 * | 3/2008 | Restorff | H01G 9/02 361/508 |
| 2008/0232029 A1 * | 9/2008 | Ning | H01G 9/145 361/503 |
| 2009/0273885 A1 * | 11/2009 | Jiang | C25F 3/04 361/508 |
| 2010/0268292 A1 * | 10/2010 | Eidelman | H01G 9/012 607/5 |
| 2010/0318142 A1 * | 12/2010 | Chen | H01G 9/045 607/5 |
| 2012/0179217 A1 * | 7/2012 | Bates | 607/5 |

FOREIGN PATENT DOCUMENTS

| | | |
|---|---|---|
| GB | 760761 | 11/1956 |
| GB | 1055362 | 1/1967 |
| GB | 2036432 A | 6/1980 |
| JP | S56-169534 U | 12/1981 |
| JP | S57-099720 | 6/1982 |
| JP | S58-155829 U | 10/1983 |
| JP | 02066920 A * | 3/1990 |
| JP | 41921/91 U | 4/1991 |
| JP | 05234814 A * | 9/1993 |
| JP | H09-326327 A | 12/1997 |
| WO | 2010/121018 A2 | 10/2010 |

* cited by examiner

HERMETICALLY SEALED ELECTROLYTIC CAPACITOR

CROSS REFERENCE TO RELATED APPLICATIONS

This application claims priority to U.S. Application No. 61/439,692 filed on Feb. 4, 2011 and PCT application No. PCT/US2012/023796 filed Feb. 3, 2012, which are incorporated by reference as if fully set forth.

FIELD OF THE INVENTION

The present invention relates to capacitors, and more specifically to a capacitor suitable for use in medical applications such as implantable cardioverter defibrillators.

BACKGROUND

Capacitors are used in a wide range of electronic applications. Certain applications require a capacitor which is capable of a rapid electrical charge to a pre-determined voltage and, once charged, is also capable of delivering sizeable pulses of energy. One example of such an application is in implantable devices. In such an application, it is also important that the capacitor be compact in size and highly reliable. Existing designs do not maximize useable space within the case for the internal structures such as the anode element, and thus require a larger case to achieve the same electronic performance.

SUMMARY

A hermetically sealed capacitor and method of manufacturing are provided. The hermetically sealed capacitor includes an anode element having an anode lead and a feed through barrel, a cathode element, a first case portion having a first opening portion and a second case portion having a second opening portion. The first and second opening portions form an opening configured to mate with the feed through barrel. The first opening portion may include a slot portion configured to receive the feed though barrel. The first and second opening portions may include first and second mating portions respectively, the first and second mating portions being configured to mate with the feed through barrel.

The feed through barrel may have a round outer surface and the first and second mating portions may each have a half round profile and a radius selected to mate with the outer surface of the feed through barrel. The first case portion and second case portion may be hermetically sealed together. The first case portion may have a first depth and the second case portion may have a second depth such that the first and second mating portions are disposed at the first and second depths respectively so as to form an opening configured to mate with the feed through barrel. The second case portion may include a protrusion, the second mating portion being formed in the protrusion. The feed through barrel may comprise glass or ceramic.

The anode element may include a protective wrap. The first and second case portions may be joined by conventional methods such as welding. The hermetically sealed capacitor may also include a metal substrate forming the cathode element. The metal substrate may be part of at least one of the first and second case portions. The metal substrate may have an alloy layer formed with a noble metal and a noble metal/base metal electrode element layer electrochemically deposited thereon. The metal substrate may comprise a valve metal. The metal substrate may comprise tantalum, niobium, hafnium, zirconium, titanium or alloys thereof.

The hermetically sealed capacitor may also include an electrolytic solution disposed between the first and second case portions. The electrolytic solution may comprise water, inorganic acids (phosphoric and boric), an organic acid (oxalic) and an organic solvent. The hermetically sealed capacitor is adapted to store energy and may provide pulse delivery of at least 80 percent of the stored energy.

An implantable device such as an implantable cardioverter defibrillator (ICD) may be configured to use the hermetically sealed wet electrolytic capacitor. The implantable device may include a battery, a processor coupled to the battery, and a capacitor coupled to the battery and the processor. The capacitor may include an anode element having an anode lead and a feed through barrel, a cathode element and a hermetically sealed case comprising a first case portion having a first opening portion and a second case portion having a having a second opening portion, the first and second opening portions forming an opening configured to mate with the feed through barrel. The capacitor is configured to store energy and the processor is configured to control a pulse delivery of at least a portion of the stored energy.

DETAILED DESCRIPTION OF THE PREFERRED EMBODIMENT

The present invention is now described with respect to a particular embodiment. That which is shown is merely for purposes of illustration and example, and one skilled in the art will understand that the present invention contemplates other options, alternatives, or variations.

Figure 1A:
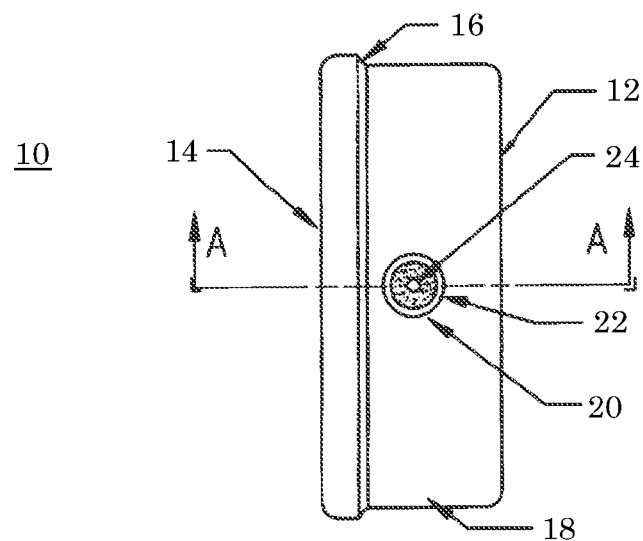
FIG. 1A is a end view of a hermetically sealed capacitor of a first embodiment.

FIG. 1A is an end view of a hermetically sealed capacitor 10 in a first embodiment. The capacitor includes a first case portion 12 and a second case portion 14. The first and second case portions 12, 14 may be joined via conventional methods such a weld 16. The first case end 18 includes an opening 20 configured to receive a feed through barrel 22. The feed through barrel 22 is generally sealed to the first case portion 12 and provides electrical insulation between the anode wire 24 and the first case portion 12.

Figure 1B:
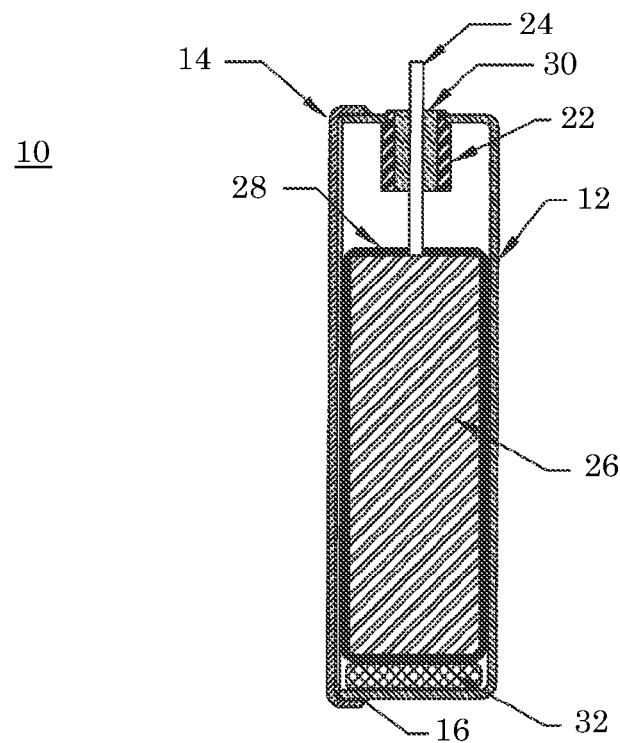
FIG. 1B is a side sectional view of the hermetically sealed capacitor taken across section A-A as shown in FIG. 1A.

FIG. 1B is a side sectional view of the hermetically sealed capacitor 10 taken across section A-A as shown in FIG. 1A. The capacitor 10 includes an anode element 26 with an anode wire 24. The anode element 26 may be constructed using a variety of methods and may include a protective wrap 28. The anode wire 24 is insulated from the first case portion 12 via feed through barrel 22. Feed through barrel 22 may include glass insulation 30. A polymeric cradle 32 is used to fill unused space between the anode element 26 and the first case portion 12. The polymeric cradle 32 may be formed using a variety of methods.

Figure 1C:
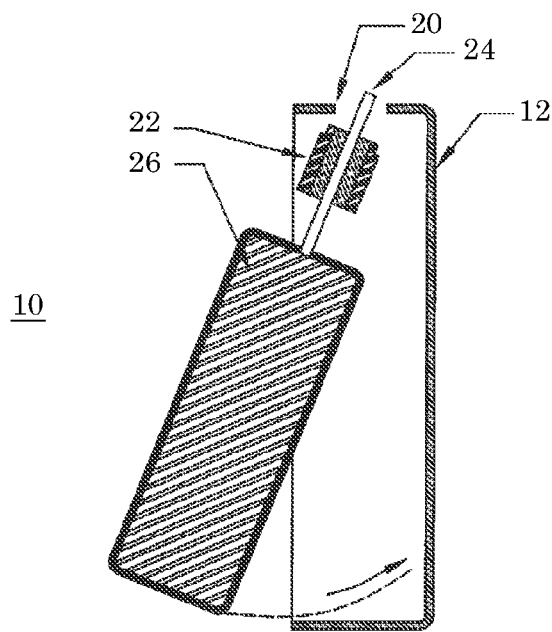
FIG. 1C is a side sectional view of the hermetically sealed capacitor showing installation of the anode element.
Figure 1D:
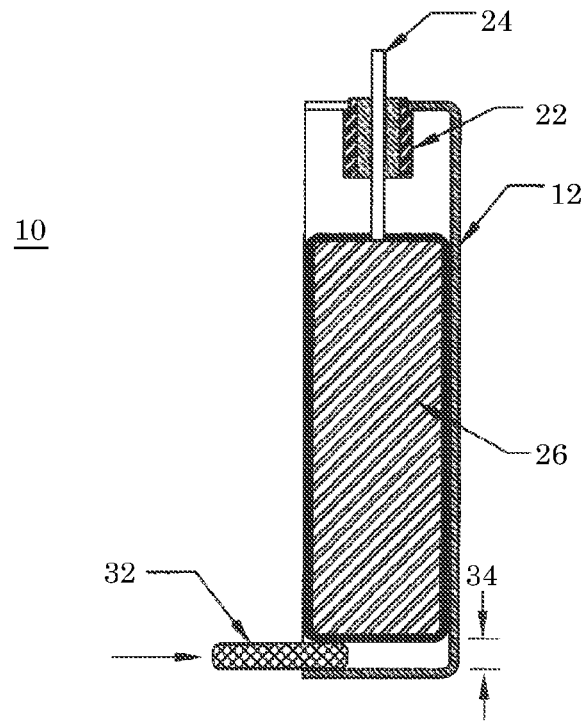
FIG. 1D is a side sectional view of the hermetically sealed capacitor showing installation of the polymeric cradle.

FIG. 1C is a side sectional view of the hermetically sealed capacitor 10 showing installation of the anode element 26. During installation, the anode element 26 is generally disposed at an angle with respect to the bottom of the first case portion 12. The feed through barrel 22 and anode wire 24 are inserted into the opening 20 in the first case portion 12. The anode element 26 is then pivoted into the first case portion such that the feed through barrel 22 is received in the opening 20. The first case portion is provided with a gap 34 to provide clearance during insertion of the anode element 26. FIG. 1D is a side sectional view 10 showing installation of the polymeric cradle 32 to fill the gap 34 between the anode element 26 and the first case portion 12.

Figures 2A, 2B:
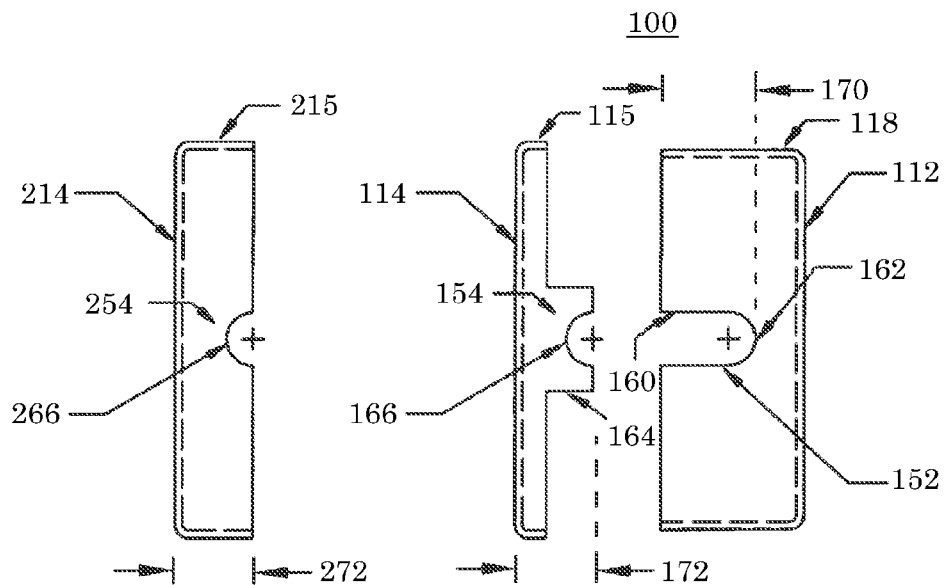
FIG. 2A is an end view of hermetically sealed capacitor of a second embodiment.
FIG. 2B is an end view of alternative embodiment of a second case portion.

FIG. 2A is an end view of a hermetically sealed capacitor 100 in accordance with a second embodiment. The capacitor 100 includes a first case portion 112 and a second case portion 114. The first and second case portions 112, 114 may be joined via conventional methods, for example welding, gluing or brazing. The first case portion 112 and the second case portion 114 are both configured to define an opening for an anode wire 124 and feed through barrel 122. The first case portion 112 has an end 118 that includes a first opening portion 152.

The first opening portion 152 is configured to allow for linear insertion of an anode element (e.g., without the need for rotation of the anode with respect to the first case portion 112). In this example, the first opening portion 152 generally includes a slot portion 160 and a first mating portion 162. The first mating portion 162 is disposed at a first depth 170. In this example, the first mating portion 162 is generally shown has a half round shape having a radius selected to mate with a round feed through barrel. It should be understood that other shapes may be used (e.g., depending on the profile of the feed through barrel) without departing from the scope of the disclosure.

The second case portion 114 has an end 115 that is formed with a second opening portion 154 disposed at a second depth 172. The second opening portion 154 also includes a second mating portion 166 formed in a protrusion 164. In this example, the second mating portion 166 is generally shown has a half round shape having a radius selected to mate with a round feed through barrel. As discussed above, other shapes may be used (e.g., depending on the profile of the feed through barrel) without departing from the scope of the disclosure. It should be understood that the first and second case portions 112, 114 are generally joined together to form a capacitor case 117 (see e.g., FIG. 2D). The first and second depths 170, 172 are selected so that the first and second mating portions 162, 166 cooperatively define an opening for a feed through barrel.

FIG. 2B shows an alternate configuration for a second case portion 214. The second case portion 214 has an end 215 that is formed with a second opening portion 254 disposed at a second depth 272. The second opening portion 254 also includes a second mating portion 266. The case end 215 is formed with sufficient depth such that the second mating portion 256 is formed in the end 215 (e.g., a protrusion is not required). In this example, the second mating portion 266 is generally shown has a half round shape having a radius selected to mate with a round feed through barrel. As discussed above, other shapes may be used (e.g., depending on the profile of the feed through barrel) without departing from the scope of the disclosure. It should be understood that a variety of case end configurations can be used to properly locate the first and second mating portions without departing from the scope of the disclosure.

Figure 2C:
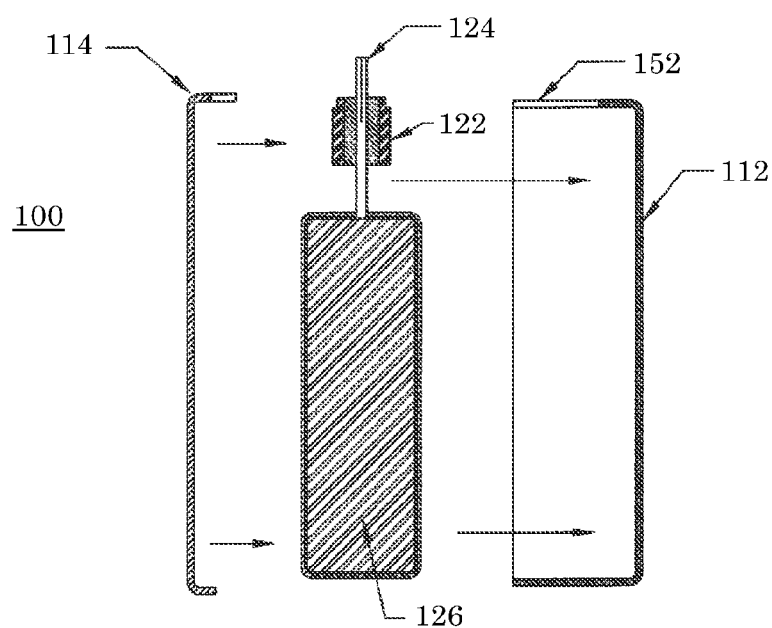
FIG. 2C is a side sectional view of the hermetically sealed capacitor showing installation of the anode element.

FIG. 2C is a side sectional view of the hermetically sealed capacitor 100 showing installation of the anode element 126. During installation, the anode element 126 is linearly inserted into the first case portion 112. The feed through barrel 122 and anode wire 124 are inserted into the first opening portion 152 without the need angular insertion or any pivoting motions. Since the anode element 126 is inserted linearly, the first case portion 112 can closely conform to the shape of the anode element 126. A large gap between the first case portion 112 and the anode element 126 is not required. Since only minimal clearance is required, a polymeric cradle is not required to fill any gaps between the first case portion 112 and the anode element 124. As a result, a larger anode 126 may be inserted into the first case portion 112.

Figure 2D:
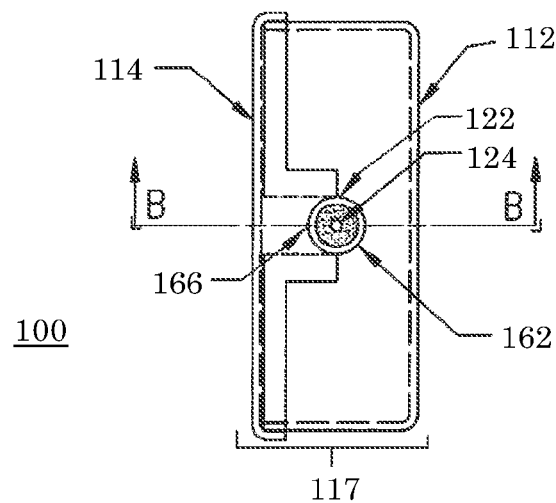
FIG. 2D is an end view of an assembled hermetically sealed capacitor.
Figure 2E:
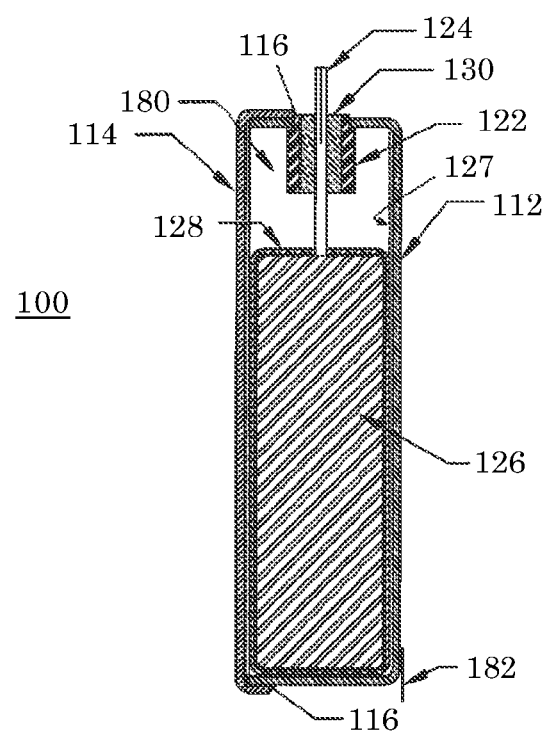
FIG. 2E is a side section view of the hermetically sealed capacitor.

FIG. 2D is an end view of an assembled hermetically sealed capacitor 100. FIG. 2E is a side section view of the hermetically sealed capacitor 100 taken along section B-B. The first and second mating portions 162, 266 work in concert to generally form an opening 220 in the capacitor case 117. In this example, the opening 220 is circular and has a radius selected to mate with a round feed through barrel 122. The first and second case portions 112, 114 may be joined via aforementioned conventional methods (shown in FIG. 2E as a weld 116) located at the junction of the first and second case portions 112, 114 (FIG. 2E). It should be understood that the entire joint between the first case portion 112 and second case portion 114 may be sealed. The feed through barrel 122 is generally sealed to the first and second case portions 112 and 114 and provides electrical insulation between the anode lead 124 and the first and second case portions 112, 114.

The anode element 126 may include a protective wrap 128. The feed through barrel 122 may include glass insulation 130. The anode element 126 may be constructed using sodium reduced capacitor grade tantalum powder pressed to a green density of between 5.0 and 7.0 grams/cc, then vacuum sintered between 1450° C. and 1650° C. Powder, press and sinter conditions may be varied to attain the requisite desired capacitance. Formation of the anode element 126 may be in an electrolyte capable of sustaining the voltage necessary for the required oxide thickness.

The capacitor 100 may have a variety of case shapes including, but not limited to, rectangular, circular or semi-circular. The capacitor 100 generally includes an anode terminal or anode wire 124 and a cathode terminal 182. An electrolytic solution 180 is disposed within the hermetically sealed case 112, 114 and surrounds both the cathode element 127 and the anode element 126.

The electrolytic solution 180 may include a gel which includes deionized (DI) water, organic and inorganic acids and an organic solvent. The constituent components of the electrolytic solution 180 may be admixed in a variety of concentrations to provide conductivity within a preferred range between 10 and 60 mS/cm. One example of such an electrolytic solution 22 would be:

65-80% DI water
0.2-0.6% phosphoric acid
15-30% ethylene glycol
3-6% oxalic acid
2-4% boric acid Referring to FIG. 2E, the cathode element 127 may be formed via a variety of methods. For example, the cathode element 127 may be formed from a metal substrate having an alloy layer formed with a noble metal and a noble metal/base metal electrode element layer electrochemically deposited on the alloyed surface from a solution of the metal salts. One example design for the cathode 18 may be a mixture of Pd and Cu electrodeposited on a Ti—Pd alloy. To increase adhesion of the cathode 18 to the alloyed substrate, an initial smooth film of Pd—Cu may be electrodeposited as a tacking layer. A rough, high surface area layer may then be deposited on top of the tacking layer to achieve a high capacitance cathode 180.

The metal substrate of the cathode element 127 may be formed of a valve metal. Examples of such valve metals include tantalum, niobium, hafnium, vanadium, zirconium, titanium or any of their alloys. The metal substrate may have any number of shapes or configurations, including a planar or cylindrical shape. The metal substrate may be a liner of any suitable shape and may represent a part of the capacitor case 112, 114. Such a construction of the cathode element 127 results in high cathode capacitance which assists in efficiently delivering energy stored in the capacitor 100 to a load.

Figure 3:
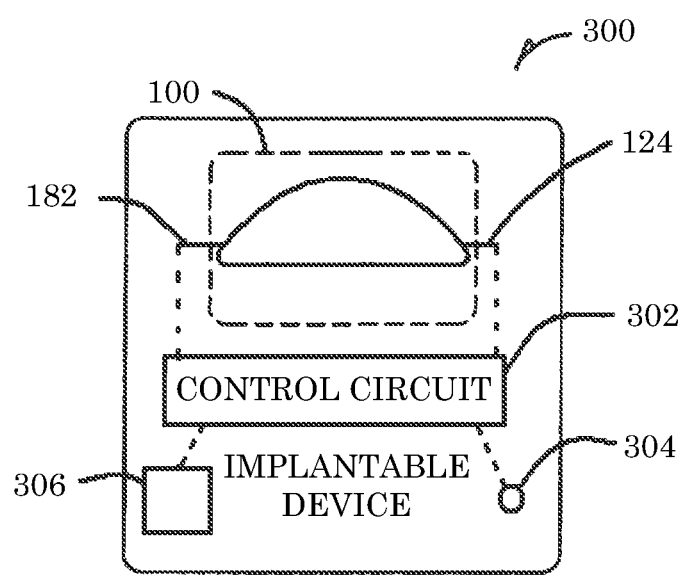
FIG. 3 is a block diagram of the capacitor of FIGS. 2A-2E in an implantable cardioverter defibrillator.

FIG. 3 illustrates one embodiment of an implantable cardioverter defibrillator (ICD) device 300. The ICD device 300 includes the capacitor 100 of FIGS. 1A-1D or FIGS. 2A-2E and a control circuit 302, which is electrically coupled to the anode and cathode terminals 124, 182 of capacitor 100. The ICD device 300 may also include a detector 304 and a battery 306. The capacitor 100 is configured to provide a pulse delivery of at least 80 percent, (but preferably greater than 87 percent), of stored energy between the first and second terminals 124, 182. The detector 304 monitors a patient's condition and provides this monitored data to the control circuit 302. The detection 304 is shown as a single element for simplicity. However, it should be understood by those of skill in the art that a plurality of detectors, monitors or detector leads may be fed into the control circuit 302 to provide patient data to the control circuit 302. The control circuit 302 monitors the information from the detector and upon detection of an anomaly or a critical condition, (which may be defined as one or more predetermined parameters that have exceeded one or more predetermined thresholds), initiates delivery of an electrical shock.

By way of example, the detector 304 may detect electrical activity in the heart of a patient and forward this data to the control circuit 302. The control circuit 304 monitors this electrical activity and if it drops below a certain electrical threshold, or if the electrical activity becomes irregular, (as happens with an arrhythmia), initiates delivery of an electrical shock.

The battery 306 may be used to charge the capacitor 100 and to power the ICD device 300. The charging of the capacitor 100 may be constant, (to counter the effects of charge leakage), such that the capacitor 100 is always ready for immediate discharge; may be periodic (i.e. charging at predetermined intervals to keep the charge level of the capacitor 100 above a predetermined threshold); or may be on demand, such that when the onset of an anomaly is detected, the battery 306 is used to charge the capacitor at that time.

In the application of an ICD device 300, the capacitor 100 performs the function of delivering electrical shock therapy into the heart of a patient when control circuit 302 detects an anomaly or a critical condition in the patient. The capacitor 100 is capable of providing a rapid electrical charge to a pre-determined voltage, and thereafter delivering one or more pulses of sufficient energy to restore normal functions of a patient's heart.

The capacitor 100 as shown in FIG. 3 is efficient in nature and highly compact and may be shaped to fit within a limited volume within an ICD device 300. In one embodiment, the size of the capacitor 100 is 1.5-3.0 CC, and comprises a half-moon shape as shown in FIG. 3, although this should not be construed to be limiting to the present invention. It should be understood that capacitor 100 may conform to any size and shape in order to fit the particular configuration demanded by the person within whom it is being implanted.

In order to support the application of an ICD device 300, the capacitor 100 may be able to supply a minimum of 9 J, (but may supply as much as 12 J), upon demand. The amount of energy actually delivered is determined by the control circuit 302.

Figure 4:
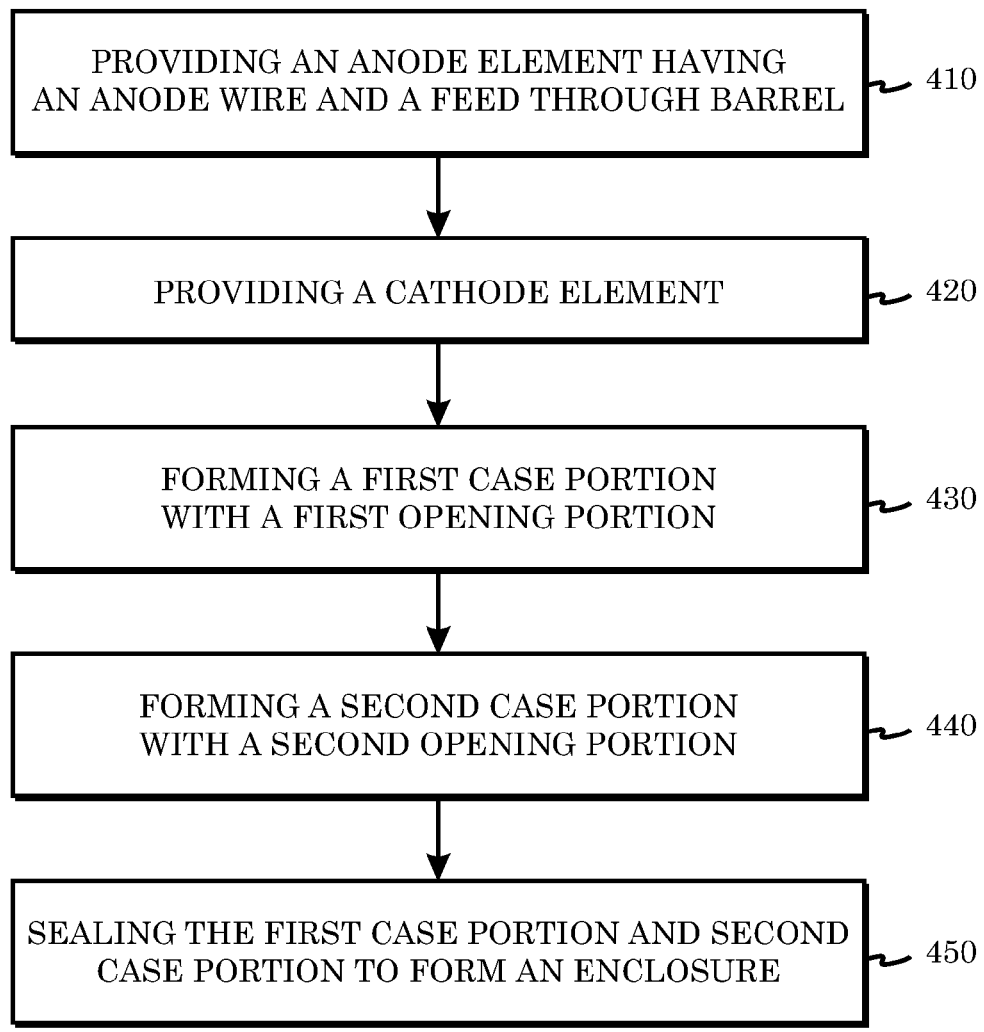
FIG. 4 is a flow diagram of a method of manufacturing a capacitor.

FIG. 4 is a flow diagram of a method 400 of manufacturing a capacitor. Method 400 includes providing an anode element having an anode wire and a feed through barrel at step 410, providing a cathode element at step 420, forming a first case portion having a first opening portion at step 430, forming a second case portion having a second opening portion at step 440, the first and second opening portions forming an opening configured to mate with the feed through barrel, and hermetically sealing (450) the first case portion and second case portion to form a case that encloses the anode and cathode elements. Sealing may include welding the first and second case portions to hermetically seal the case. The case may be at least partially filled with an electrolytic solution.

Method 400 may include forming a slot portion in the first opening portion, the slot portion being configured to receive the feed though barrel. Method 400 may include forming first and second mating portions in the first and second opening portions respectively, the first and second mating portions being configured to mate with the feed through barrel. Method 400 may include forming first and second mating portions each having a half round profile and a radius selected to mate with an outer surface of the feed through barrel. Further, method 400 may include forming a protrusion in the second case portion, the second mating portion being formed in the protrusion. Method 400 may include at least partially encapsulating the anode element with a protective wrap.

A hermetically sealed wet electrolytic capacitor has been described. The present invention is not to be limited to the specific embodiment shown or described herein as the present invention contemplates variations in the size and shape of the capacitor, variations in the materials used, and other variations, alternatives, and options as would be apparent to one skilled in the art.

What is claimed is:
1. A hermetically sealed capacitor, comprising:
a single tantalum anode element comprising a pressed powder and having a bottom surface, a top surface, and side surfaces and further having an anode wire extending from the top surface;

a feedthrough barrel surrounding at least a portion of the anode wire and including an insulating material;
a cathode element electrically distal to the anode element;
a first case portion, a first opening portion formed in an edge of the first case portion and comprising a first mating portion, a slot formed adjacent the first mating portion, the slot extending a depth into the edge of the first case portion, the depth being longer than a radius of the feed through barrel, the anode positioned in the first case portion adjacent the bottom surface, the first case portion closely conforming to the shape of the anode element at the bottom surface and the side surfaces, the first case portion configured to allow for linear insertion of the anode element;
a second case portion having a top surface, a bottom surface and side surfaces, the top surface including a protrusion extending from an edge of the top surface, a second opening portion formed in the protrusion and comprising a second mating portion, the top surface of the second case portion being adjacent the top surface of the anode when the anode is positioned in the casing, the protrusion configured to rest against an outer surface of the first case portion when the first case portion and second case portions are joined;
the first and second case portions forming an enclosure for the anode and cathode elements and at least parts of the feed through barrel and an opening formed by the first and second mating portions configured to mate with the feed through barrel;
wherein the feed through barrel is sealed to the first mating portion and the second mating portion.

2. The hermetically sealed capacitor of claim 1 wherein the feed through barrel has a round outer surface and the first and second mating portions each have a half round profile and a radius selected to mate with the outer surface of the feed through barrel.

3. The hermetically sealed capacitor of claim 1 wherein the first case portion has a first depth and the second case portion has a second depth and the first and second mating portions are disposed at the first and second depths respectively so as to form an opening configured to mate with the feed through barrel.

4. The hermetically sealed capacitor of claim 1 wherein the insulating material comprises glass or ceramic.

5. The hermetically sealed capacitor of claim 1 wherein the anode element includes a protective wrap.

6. The hermetically sealed capacitor of claim 1 wherein the first and second case portions are joined by welding.

7. The hermetically sealed capacitor of claim 1 further comprising a metal substrate forming the cathode element.

8. The hermetically sealed capacitor of claim 7 wherein the metal substrate is part of at least one of the first and second case portions.

9. The hermetically sealed capacitor of claim 7 wherein the metal substrate has an alloy layer formed with a noble metal and a noble metal/base metal electrode element layer electrochemically deposited thereon.

10. The hermetically sealed capacitor of claim 7 wherein the metal substrate comprises a valve metal.

11. The hermetically sealed capacitor of claim 7 wherein the metal substrate comprises tantalum, niobium, hafnium, zirconium, titanium or alloys thereof.

12. The hermetically sealed capacitor of claim 1 further comprising an electrolytic solution disposed between the first and second case portions.

13. The hermetically sealed capacitor of claim 12 wherein the electrolytic solution comprises water, inorganic acids, an organic acid and an organic solvent.

14. The hermetically sealed capacitor of claim 13, wherein the inorganic acids are phosphoric and boric acids and the organic acid is oxalic acid.

15. The hermetically sealed capacitor of claim 1 being adapted to store energy and to provide pulse delivery of at least 80 percent of the stored energy.

16. The hermetically sealed capacitor of claim 1 further comprising a control circuit electrically coupled to the anode and cathode elements, the control circuit being configured as an implantable cardioverter defibrillator (ICD).

17. An implantable device including:
a battery;
a processor coupled to the battery; and
a capacitor coupled to the battery and the processor, the capacitor including;
  a single tantalum anode element comprising a pressed powder and having a bottom surface, a top surface and side surfaces and further having an anode wire extending from the top surface;
  a feed through barrel surrounding at least a portion of the anode wire and including an insulating material;
  a cathode element electrically distal to the anode element; and
  a hermetically sealed case having:
    a first case portion, a first opening portion formed in an edge of the first case portion and comprising a first mating portion, a slot formed adjacent the first mating portion, the slot extending a depth into the edge of the first case portion, the depth being longer than a radius of the feed through barrel, and
    a second case portion having a top surface, a bottom surface and side surfaces, the top surface including a protrusion extending from an edge of the top surface, a second opening portion formed in the protrusion and comprising a second mating portion, the top surface of the second case portion being adjacent the top surface of the anode when the anode is positioned in the casing, the protrusion configured to rest against an outer surface of the first case portion when the first case portion and second case portions are joined;
    the anode positioned in the first case portion adjacent the bottom surface, the first case portion closely confirming to the shape of the anode element at the bottom and side surfaces, the first case portion configured to allow for linear insertion of the anode element, the first and second opening portions forming an opening configured to mate with the feed through barrel, the feed through barrel being sealed to the first mating portion and the second mating portion;
  the capacitor being configured store energy, the processor being configured to control a pulse delivery of at least a portion of the stored energy.

18. The implantable device of claim 17, wherein the implantable device is an implantable cardioverter defibrillator (IDC).

19. A method of manufacturing a capacitor, comprising:
providing a single tantalum anode element comprising a pressed powder and having a bottom surface, a top surface and side surfaces and further having an anode wire extending from the top surface;

providing a feed through barrel surrounding at least a portion of the anode wire and including an insulating material;

providing a cathode element electrically distal to the anode element;

forming a first case portion, a first opening portion formed in an edge of the first case portion and comprising a first mating portion with a slot adjacent the first mating portion, the slot extending a depth into the edge of the first case portion, the depth being longer than a radius of the feed through barrel;

forming a second case portion having a top surface, a bottom surface and side surfaces, the top surface including a protrusion extending a particular distance from an edge of the top surface, a second opening portion formed in the protrusion and comprising a second mating portion, the protrusion configured to rest against an outer surface of the first case portion when the first case portion and second case portions are joined, the top surface of the second case portion being adjacent the top surface of the anode when the anode is positioned in the casing, the first and second opening portions forming an opening configured to mate with the feed through barrel;

hermetically sealing the first case portion and second case portion to form a case that encloses the anode and cathode elements and at least parts of the feed through barrel, wherein the anode is positioned in the case adjacent the bottom surface of the first case portion, the first case portion closely conforming to the shape of the anode element at the bottom surface and the side surfaces, the first case portion configured to allow for linear insertion of the anode element; and sealing the feed through barrel to the first mating portion and the second mating portion.

20. The method of claim 19, wherein the first and second mating portions each have a half round profile and a radius selected to mate with an outer surface of the feed through barrel.

21. The method of claim 19, wherein the first case portion has a first depth and the second case portion has a second depth and the first and second mating portions are disposed at the first and second depths respectively so as to form an opening configured to mate with the feed through barrel.

22. The method of claim 19 further comprising at least partially encapsulating the anode element with a protective wrap.

23. The method of claim 19 further comprising welding the first and second case portions to hermetically seal the case.

24. The method of claim 19, further comprising a metal substrate forming the cathode element, wherein the metal substrate is part of at least one of the first and second case portions.

25. The method of claim 24 wherein the metal substrate has an alloy layer formed with a noble metal and a noble metal/base metal electrode element layer electrochemically deposited thereon.

26. The method of claim 24 wherein the metal substrate comprises a valve metal.

27. The method of claim 24 wherein the metal substrate comprises tantalum, niobium, hafnium, zirconium, titanium or alloys thereof.

28. The method of claim 19 further comprising at least partially filling the case with an electrolytic solution.

29. The method of claim 19 wherein the electrolytic solution comprises water, inorganic acids, an organic acid and an organic solvent.

30. The method of claim 29, wherein the inorganic acids are phosphoric and boric acids and the organic acid is oxalic acid.

\* \* \* \* \*